United States Patent
Ezoe et al.

(10) Patent No.: US 7,563,624 B2
(45) Date of Patent: Jul. 21, 2009

(54) MEASUREMENT METHOD USING BIOSENSOR

(75) Inventors: Toshihide Ezoe, Kanagawa (JP); Koji Kuruma, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 400 days.

(21) Appl. No.: 11/475,108

(22) Filed: Jun. 27, 2006

(65) Prior Publication Data
US 2007/0020688 A1    Jan. 25, 2007

(30) Foreign Application Priority Data
Jun. 30, 2005  (JP)  ............................ 2005-191265

(51) Int. Cl.
*G01N 33/553* (2006.01)
(52) U.S. Cl. ................ 436/525; 422/82.11; 435/287.2; 435/288.7; 435/174; 435/176; 436/164; 436/165; 436/524; 436/805
(58) Field of Classification Search ........................ None
See application file for complete search history.

(56) References Cited

U.S. PATENT DOCUMENTS

| | | | | | |
|---|---|---|---|---|---|
| 4,240,889 | A | * | 12/1980 | Yoda et al. | 204/403.09 |
| 4,844,613 | A | * | 7/1989 | Batchelder et al. | 356/318 |
| 6,808,938 | B2 | * | 10/2004 | Hamalainen et al. | 436/518 |
| 2005/0181497 | A1 | | 8/2005 | Saito et al. | |
| 2006/0003395 | A1 | | 1/2006 | Yamamoto et al. | |

FOREIGN PATENT DOCUMENTS

EP    1 293 779 A2    3/2003
EP    1 538 436 A1    6/2005

OTHER PUBLICATIONS

Johnsson B. et al "Immobilization of Proteins to a Carboxymethyldextran-Modified Gold Surface for Biospecific Interaction Analysis in Surface Plasmon Resonance Sensors" Analytical Biochemistry, vol. 198, No. 2, pp. 268-277, 1991.
Brynda E. et al "Immobilisation of Multilayer Bioreceptor Assemblies on Solid Substrates" Biosensors and Bioelectronics, vol. 13, No. 2, pp. 165-172, 1998.
Schlereth D. et al "Self-assembled Monolayers with Biospecific Affinity for NAD(H)-dependent dehydrogenases: Characterization by Surface Plasmon Resonance Combined with Electrochemistry 'in situ'" Journal of Electroanalytical Chemistry, vol. 444, No. 2, pp. 231-240, 1998.
Houseman B. et al "The Role of Ligand Density in the Enzymatic Glycosylation of Carbohydrates Presented on Self-Assembled Monolayers of Alkanethiolates on Gold" Angewandte Chemie. International Edition, vol. 38, No. 6, pp. 782-785, 1999.

* cited by examiner

*Primary Examiner*—Christopher L Chin
(74) *Attorney, Agent, or Firm*—Sughrue Mion, PLLC

(57) ABSTRACT

It is an object of the present invention to provide a method for carrying out on a same biosensor both of the measurement of the amount of a physiologically active substance immobilized on a biosensor substrate and the measurement of the biological activity of the above physiologically active substance, thereby analyzing the interaction of a substance with the above physiologically active substance that maintains its activity. The present invention provides a measurement method using a biosensor substrate, wherein both the amount of a physiologically active substance immobilized on the substrate and the biological activity of the physiologically active substance immobilized on the substrate are measured on said same biosensor substrate.

10 Claims, 1 Drawing Sheet

MEASUREMENT METHOD USING BIOSENSOR

TECHNICAL FIELD

The present invention relates to a measurement method using a biosensor. More specifically, the present invention relates to a method for carrying out on a same biosensor the measurement of the amount of a physiologically active substance immobilized on a biosensor substrate and the measurement of the biological activity of the above physiologically active substance.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

A commonly used measurement chip in the surface plasmon resonance (SPR) analysis comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules. As a thin film having a functional group capable of immobilizing a physiologically active substance, there has been reported a measurement chip where a physiologically active substance is immobilized by using a functional group binding to metal, a linker with a chain length of 10 or more atoms, and a compound having a functional group capable of binding to the physiologically active substance (Japanese Patent No. 2815120). Moreover, a measurement chip comprising a metal film and a plasma-polymerized film formed on the metal film has been reported (Japanese Patent Laid-Open No. 9-264843).

As stated above, in the conventional surface plasmon resonance (SPR) measurement, a substance interacting with a physiologically active substance immobilized on a measurement chip has been detected or measured. However, since the biological activity of the physiologically active substance immobilized on a measurement chip has not been measured, the interaction of the above substance with the physiologically active substance has not necessarily been measured in a state where activity that should have been essentially observed has been maintained.

DISCLOSURE OF THE INVENTION

It is an object of the present invention to solve the aforementioned problem of the prior art technique. That is to say, it is an object of the present invention to provide a method for carrying out on a same biosensor both of the measurement of the amount of a physiologically active substance immobilized on a biosensor substrate and the measurement of the biological activity of the above physiologically active substance, thereby analyzing the interaction of a substance with the above physiologically active substance that maintains its activity.

As a result of intensive studies directed towards achieving the aforementioned objects, the present inventors have found that the measurement of the amount of a physiologically active substance immobilized on a biosensor substrate and the measurement of the biological activity of the above physiologically active substance are carried out on a same (single) biosensor, so as to achieve the aforementioned objects, thereby completing the present invention.

The present invention provides a measurement method using a biosensor substrate, wherein both the amount of a physiologically active substance immobilized on the substrate and the biological activity of the physiologically active substance immobilized on the substrate are measured on said same biosensor substrate.

Preferably, the physiologically active substance is a protein. More preferably, the physiologically active substance is an enzyme.

Preferably, the amount of the physiologically active substance immobilized on the substrate is measured by surface plasmon resonance analysis.

Preferably, the surface plasmon resonance analysis is carried out using a biosensor used for a surface plasmon resonance measurement device comprising a dielectric block, a metal film formed on a face of the dielectric block, a light source for generating a light beam, an optical system for allowing said light beam to enter said dielectric block such that total reflection conditions can be obtained at the interface between said dielectric block and said metal film and that components at various incident angles can be contained, and a light-detecting means for detecting the state of surface plasmon resonance by measuring the intensity of the light beam totally reflected at said interface, wherein said biosensor is composed of said dielectric block and said metal film, wherein said dielectric block is formed as one block comprising the entirety of the entrance face and exit face of said light beam and a face on which said metal film is formed, and said metal film is integrated with the dielectric block.

Preferably, the biological activity of the physiologically active substance is measured by spectroscopic measurement Preferably, the measurement method according to the present invention comprises:

(1) a step of confirming the biological activity value per unit quantity of a physiologically active substance immobilized on a substrate, which is represented by the following formula 1, based on the amount of the physiologically active substance immobilized on the substrate and the biological activity value of the physiologically active substance immobilized on said substance, which are measured on the same biosensor substrate, (biological activity value per unit quantity of physiologically active substance immobilized)=(biological activity value of physiologically active substance immobilized on substrate)/(amount of physiologically active substance immobilized on substrate);   Formula 1 and (2) a step of detecting or measuring the interaction of the physiologically active substance with a test substance using the substrate on which the physiologically active substance has been immobilized by the immobilization method confirmed in said step (1).

Preferably, the measurement method according to the present invention comprises:

(1) a step of optimizing a method of immobilizing a physiologically active substance on a biosensor substrate, using, as an indicator, the biological activity value per unit quantity of the physiologically active substance immobilized on a substrate, which is represented by the following formula 1, based on the amount of the physiologically active substance immobilized on the substrate and the biological activity value of the physiologically active substance immobilized on said substance, which are measured on the same biosensor substrate, (biological activity value per unit quantity of physiologically active substance immobilized)=(biological activity value of physiologically active substance immobilized on substrate)/(amount of physiologically active substance immobilized on substrate);   Formula 1 and (2) a step of detecting or measuring the interaction of the physiologically active substance with a test substance, using the substrate on which the physiologically active substance has been immobilized by the immobilization method optimized in said step (1).

Preferably, the measurements of the amount of a physiologically active substance immobilized on a substrate and the biological activity value of the physiologically active substance immobilized on said substrate in step (1), and the detection or measurement of the interaction of the physiologically active substance with a test substance in step (2), are carried out on the same biosensor substrate.

BEST MODE FOR CARRYING OUT THE INVENTION

Figure 1:
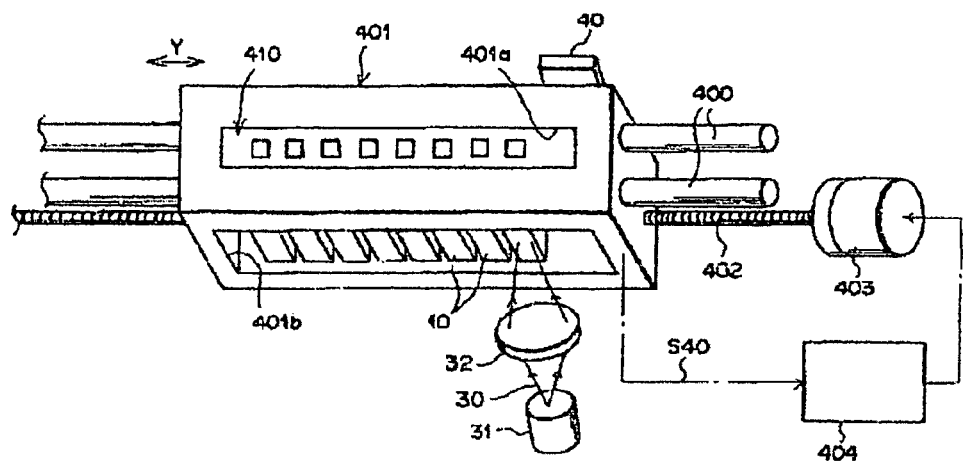
FIG. 1 shows the plasmon resonance measurement device.

Embodiments of the present invention will be described below.

The present invention relates to a measurement method using a biosensor wherein a physiologically active substance was immobilized on a substrate, which is characterized in that the measurement of the amount of the physiologically active substance immobilized on the biosensor substrate and the measurement of the biological activity of the physiologically active substance are carried out on the aforementioned same biosensor. In the present invention, the measurement of a physiologically active substance immobilized and the measurement of the biological activity of the physiological active substance are carried out on a same biosensor, so that the physiologically active substance can be immobilized in the most ideal state before conducting the measurement of the interaction of the physiologically active substance with a test substance. Thus, the interaction of the physiologically active substance with the test substance can be accurately measured.

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

In the biosensor used in the present invention, a metal surface or metal film can be used as a substrate. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and is more preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and have excellent workability are preferably used.

Preferably in the present invention, the substrate is a metal surface or metal film coated with a hydrophobic polymer or a hydrophilic polymer, or a metal surface or metal film having a self assembled membrane. The hydrophobic polymer, hydrophilic polymer, and self assembled membrane are mentioned below.

The hydrophobic polymer used in the present invention is a polymer having no water-absorbing properties. Its solubility in water (at 25° C.) is 10% or less, more preferably 1% or less, and most preferably 0.1% or less.

A hydrophobic monomer which forms a hydrophobic polymer can be selected from vinyl esters, acrylic esters, methacrylic esters, olefins, styrenes, crotonic esters, itaconic diesters, maleic diesters, fumaric diesters, allyl compounds, vinyl ethers, vinyl ketones, or the like. The hydrophobic polymer may be either a homopolymer consisting of one type of monomer, or copolymer consisting of two or more types of monomers.

Examples of a hydrophobic polymer that is preferably used in the present invention may include polystyrene, polyethylene, polypropylene, polyethylene terephthalate, polyvinyl chloride, polymethyl methacrylate, polyester, and nylon.

A substrate is coated with a hydrophobic polymer according to common methods. Examples of such a coating method may include spin coating, air knife coating, bar coating, blade coating, slide coating, curtain coating, spray method, evaporation method, cast method, and dip method.

In the dip method, coating is carried out by contacting a substrate with a solution of a hydrophobic polymer, and then with a liquid which does not contain the hydrophobic polymer. Preferably, the solvent of the solution of a hydrophobic polymer is the same as that of the liquid which does not contain said hydrophobic polymer.

In the dip method, a layer of a hydrophobic polymer having an uniform coating thickness can be obtained on a surface of a substrate regardless of inequalities, curvature and shape of the substrate by suitably selecting a coating solvent for hydrophobic polymer.

The type of coating solvent used in the dip method is not particularly limited, and any solvent can be used so long as it can dissolve a part of a hydrophobic polymer. Examples thereof include formamide solvents such as N,N-dimethylformamide, nitrile solvents such as acetonitrile, alcohol solvents such as phenoxyethanol, ketone solvents such as 2-butanone, and benzene solvents such as toluene, but are not limited thereto.

In the solution of a hydrophobic polymer which is contacted with a substrate, the hydrophobic polymer may be dissolved completely, or alternatively, the solution may be a suspension which contains undissolved component of the hydrophobic polymer. The temperature of the solution is not particularly limited, so long as the state of the solution allows a part of the hydrophobic polymer to be dissolved. The temperate is preferably $-20°$ C. to $100°$ C. The temperature of the solution may be changed during the period when the substrate is contacted with a solution of a hydrophobic polymer. The concentration of the hydrophobic polymer in the solution is not particularly limited, and is preferably 0.01% to 30%, and more preferably 0.1% to 10%.

The period for contacting the solid substrate with a solution of a hydrophobic polymer is not particularly limited, and is preferably 1 second to 24 hours, and more preferably 3 seconds to 1 hour.

As the liquid which does not contain the hydrophobic polymer, it is preferred that the difference between the SP value (unit: $(J/cm^3)^{1/2}$) of the solvent itself and the SP value of the hydrophobic polymer is 1 to 20, and more preferably 3 to 15. The SP value is represented by a square root of intermolecular cohesive energy density, and is referred to as solubility parameter. In the present invention, the SP value δ was calculated by the following formula As the cohesive energy (Ecoh) of each functional group and the mol volume (V), those defined by Fedors were used (R. F. Fedors, Polym. Eng. Sci., 14(2), P147, P472(1974)).

$$\delta = (\Sigma Ecoh/\Sigma V)^{1/2}$$

Examples of the SP values of the hydrophobic polymers and the solvents are shown below;

Solvent: 2-phenoxyethanol:25.3 against polymethylmethacrylate-polystyrene copolymer (1:1):21.0

Solvent: acetonitrile:22.9 against polymethylmethacrylate: 20.3

Solvent: toluene:18.7 against polystyrene: 21.6

The period for contacting a substrate with a liquid which does not contain the hydrophobic polymer is not particularly limited, and is preferably 1 second to 24 hours, and more preferably 3 seconds to 1 hour. The temperature of the liquid is not particularly limited, so long as the solvent is in a liquid state, and is preferably $-20°$ C. to $100°$ C. The temperature of the liquid may be changed during the period when the substrate is contacted with the solvent. When a less volatile solvent is used, the less volatile solvent may be substituted with a volatile solvent which can be dissolved in each other after the substrate is contacted with the less volatile solvent for the purpose of removing the less volatile solvent.

The coating thickness of a hydrophobic polymer is not particularly limited, but it is preferably between 0.1 nm and 500 nm, and particularly preferably between 1 nm and 300 nm.

Examples of the hydrophilic polymer used in the present invention may include polyhydroxy polymers. Examples thereof may include polysaccharides (e.g. agarose, dextran, carrageenan, alginic acid, starch, and cellulose), and synthetic polymers (e.g. polyvinyl alcohol). In the present invention, polysaccharides are preferably used, and dextran is most preferable.

In the present invention, a polyhydroxy polymer having a mean molecular weight between 10,000 and 2,000,000 is preferably used. A polyhydroxy polymer having a mean molecular weight preferably between 20,000 and 2,000,000, more preferably between 30,000 and 1,000,000, and most preferably between 200,000 and 800,000, can be used.

For example, a polyhydroxy polymer is allowed to react with bromoacetic acid under basic conditions, so that it can be carboxylated. By controlling reaction conditions, a certain ratio of hydroxy groups contained in a polyhydroxy compound at an initial stage can be carboxylated. In the present invention, 1% to 90% hydroxy groups can be carboxylated, for example. The carboxylation rate of a surface coated with any given polyhydroxy polymer can be calculated by the following method. Using a di-tert-butylcarbodiimide/pyridine catalyst, the surface of a film is subjected to gas phase modification with trifluoroethanol at 50° C. for 16 hours. Thereafter, the amount of fluorine derived from trifluoroethanol is measured by ESCA (electron spectroscopy for chemical analysis), and the ratio between the amount of fluorine and the amount of oxygen on the film surface (hereinafter referred to as F/O value) is calculated. A theoretical F/O value obtained when all hydroxy groups have been carboxylated is set at 100%. Then, a F/O value obtained by carboxylation under certain conditions is measured. Thus, a carboxylation rate at that time can be calculated.

A polyhydroxy polymer can be attached to a metal film via an organic molecule $X^1—R^1—Y^1$. Such an organic molecule $X^1—R^1—Y^1$ will be described in detail.

$X^1$ is a group having ability to bind to a metal film. Specifically, asymmetrical or symmetrical sulfide (—$SSR^{11}Y^{11}$, —$SSR^1Y^1$), sulfide (—$SR^{11}Y^{11}$, —$SR^1Y^1$), diselenide (—$SeSeR^{11}Y^{11}$, —$SeSeR^1Y^1$), selenide (—$SeR^{11}Y^{11}$, —$SeR^1Y^1$), thiol (—SH), nitrile (—CN), isonitrile, nitro (—$NO_2$), selenol (—SeH), a trivalent phosphorus compound, isothiocyanate, xanthate, thiocarbamate, phosphine, thioacid, and dithioacid (—COSH, —CSSH) are preferably used.

$R^1$ (and $R^{11}$) are discontinued by hetero atoms in some cases. For a moderately dense load, these are preferably straight chains (that are not branched), and these are hydrocarbon chains containing double and/or triple bonds in some cases. Such a chain preferably has a length consisting of more than 10 atoms. A carbon chain may be perfluorinated in some cases.

$Y^1$ and $Y^{11}$ are groups for allowing a polyhydroxy polymer to bind with a metal film. $Y^1$ and $Y^{11}$ are preferably identical and have properties of capable of binding to a polyhydroxy polymer directly or after activation. Specifically, a hydroxyl, carboxyl, amino, aldehyde, hydrazide, carbonyl, epoxy, or vinyl group can be used.

Specific examples of an organic molecule $X^1$—$R^1$—$Y^1$ used herein may include 10-carboxy-1-decanethiol, 4,4'-ithiodibutyric acid, 11-hydroxy-1-undecanethiol, 16-hydroxy-1-hexadecanethiol, and 11-amino-1-undecanethiol.

A sulfur compound such as thiol or disulfide spontaneously adsorbs on a precious metal substrate such as gold, so as to provide an ultra-thin membrane with a size of a single molecule. In addition, since an aggregate thereof has a sequence that depends on the crystal lattice of a substrate or the molecular structure of an admolecule, it is called a self assembled membrane. In the present invention, 7-carboxy-1-heptanethiol, 10-carboxy-1-decanethiol, 4,4'-dithiodibutyric acid, 11-hydroxy-1-undecanethiol, 11-amino-1-undecanethiol, or the like can be used as such a self assembled membrane.

A substrate used in the present invention may further have a linker.

A specific example of the linker used in the present invention is the compound represented by the following formula (4):

wherein $X^{20}$ represents a group capable of reacting with a functional group in the hydrophobic polymer, the polyhydroxy polymer or the self-assembling membrane; $L^{20}$ represents a divalent linking group; and $Y^{20}$ represents a group capable of reacting with a compound so as to form a covalent bond.

In formula (4), $X^{20}$ represents a group capable of reacting with a functional group in the hydrophobic polymer, the polyhydroxy polymer or the self-assembling membrane. $X^{20}$ preferably represents a halogen atom, an amino group, an amino group that is protected with a protecting group, a carboxyl group, a carbonyl group having a leaving group, a hydroxyl group, a hydroxyl group that is protected with a protecting group, an aldehyde group, —$NHNH_2$, —N=C=O, —N=C=S, an epoxy group, or a vinyl group.

The term "protecting group" is used herein to mean a group that causes deprotection in a reaction system, so as to form a functional group. Examples of a protecting group for an amino group may include a tert-butyloxycarbonyl group (Boc), a 9-fluorenylmethyloxycarbonyl group (Fmoc), a nitrophenyl sulfenyl group (Nps), and a dithiasuccinyl group (Dts).

In addition, an example of a protecting group for a hydroxyl group is an acyl group.

Examples of the "leaving group" used herein may include a halogen atom, an alkoxy group, an aryloxy group, an alkylcarbonyloxy group, an arylcarbonyloxy group, a halogenated alkylcarbonyloxy group, an alkylsulfonyloxy group, a halogenated alkylsulfonyloxy group, and an arylsulfonyloxy group.

Moreover, as such a leaving group, an ester group generated as a result of the combination of carboxylic acid, known dehydrating condensing agents (for example, carbodiimides), and an N-hydroxy compound, is also preferably used.

In formula (4), $L^{20}$ represents a divalent linking group. The total atomic number of L is preferably between 2 and 1,000. Furthermore, $L^{20}$ is preferably a substituted or unsubstituted alkyl group, a substituted or unsubstituted alkyleneoxy group, a substituted or unsubstituted aryleneoxy group, or a divalent linking group wherein $X^{20}$ in formula (4) binds to $Y^{20}$ of another molecule, resulting in a continuous structure.

In formula (4), $Y^{20}$ represents a group capable of reacting with a compound so as to form a covalent bond. $Y^{20}$ is preferably a halogen atom, an amino group, an amino group that is protected with a protecting group, a carboxyl group, a carbonyl group having a leaving group, a hydroxyl group, a hydroxyl group that is protected with a protecting group, an aldehyde group, —$NHNH_2$, —N=C=O, —N=C=S, an epoxy group, or a vinyl group. As such a protecting group and a leaving group, the same groups as those described above can be used.

Specific examples of the compound represented by the formula (4) are given below. However, the compound represented by formula (4) used in the present invention is not limited thereto.

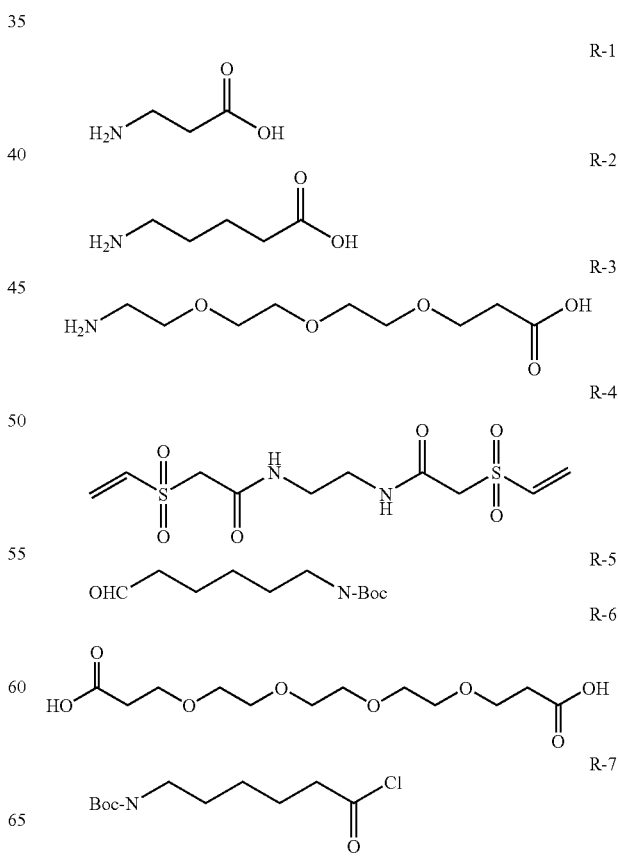

-continued

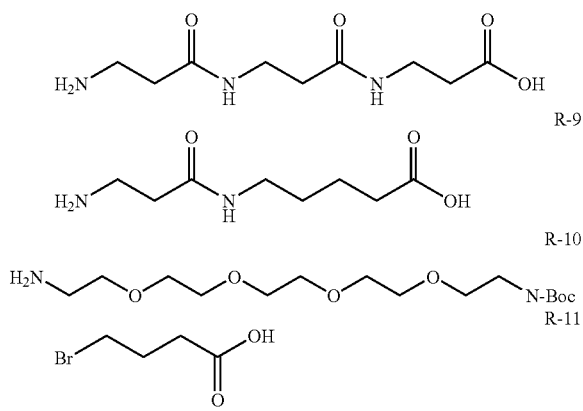

It is preferable that the biosensor of the present invention has a functional group capable of immobilizing a physiologically active substance on the outermost surface of the substrate. The term "the outermost surface of the substrate" is used herein to mean "the surface, which is farthest from the substrate," and more specifically, it means "the surface, which is farthest from the surface in a hydrophobic polymer applied on a substrate."

A physiologically active substance immobilized on the surface for the biosensor is not particularly limited, as long as it interacts with a measurement target, and it has any physiological activity. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability. Among them, protein is preferred, and enzyme is particularly preferred.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

A biosensor to which a physiologically active substance is immobilized as described above can be used to detect and/or measure a substance which interacts with the physiologically active substance.

In the present invention, it is preferable to detect and/or measure an interaction between a physiologically active substance immobilized on the surface used for a biosensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta SP$), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle ($\theta SP$) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta SP$) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle ($\theta SP$) is measured periodically when a certain period of time has elapsed.

If the test substance contained in the sample solution is bound to the sensing substance, the refractive index of the sensing substance is changed by this binding over time. Accordingly, the above attenuated total reflection angle ($\theta SP$) is measured periodically after the elapse of a certain time, and it is determined whether or not a change has occurred in the above attenuated total reflection angle ($\theta SP$), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle (θSP). For example, a sample solution may be added to a sensing substance, and the amount of an attenuated total reflection angle (θSP) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle (θSP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle (θSP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

As described above, in the measurement method of the present invention, it is possible to conform whether or not a physiologically active substance has been immobilized in a state where it has biological activity, before the detection or measurement of a substance interacting with the above physiologically active substance by means such as surface plasmon resonance analysis. When such a physiologically active substance does not have biological activity, it is preferable to optimize an immobilization method, so that the physiologically active substance exhibits biological activity. Specifically, both the amount of the physiologically active substance immobilized and the biological activity value immobilized on a substrate are measured on a same (single) substrate of a biosensor, so as to calculate the biological activity value per unit quantity of the physiologically active substance immobilized, which is represented by the following formula 1:

Biological activity value per unit quantity of physiologically active substance immobilized=(biological activity value of physiologically active substance immobilized on substrate)/(amount of physiologically active substance immobilized on substrate)     Formula 1

In the present invention, the interaction of a physiologically active substance with a test substance can be detected for measured after confirmation of the biological activity value represented by formula 1 or optimization thereof.

When an specific example of such a physiologically active substance is a protein, it is considered that a decrease in the biological activity thereof occurs as a result of a change in the three-dimensional structure of the protein due to (1) the pH of a buffer solution used for immobilization, (2) the electric charge of a protein-immobilization membrane, (3) an immobilization density, (4) formation of the covalent bond between a functional group of the protein-immobilization membrane and the protein, or the like, during immobilization of the physiologically active substance on a sensor substrate.

Accordingly, in order to improve the biological activity of a physiologically active substance, an immobilization method is determined by trial and error, using the biological activity value represented by (formula 1) as an indicator, based on the causes described in (1) to (4) above.

When the interaction of a compound with a protein is measured in a state where the three-dimensional structure of the protein has been changed and the biological activity thereof has been lost (denatured), a specific binding is not detected, but many non-specific bindings are detected. It is substantially difficult to conduct immobilization such that 100% of the immobilized proteins maintain the biological activity thereof. However, it is preferable that 50% or more of proteins have the biological activity thereof, and it is more preferable that 80% or more of proteins have the biological activity thereof.

The term "biological activity" used in the present invention may include enzyme activity, antibody activity, and receptor activity. The term "enzyme" is a genetic name of proteins having catalytic action, which smoothly promotes various chemical reactions occurring in a body, such as food digestion. The term "catalyst" generally means a substance acting as an intermediary for efficiently conducting chemical reactions.

The measurement principle of enzyme activity is described in *Tanpakushitsu, Koso no Kiso Jikken Ho* (Basic experiment methods for proteins and enzymes), Takeichi Horio, Jinpei Yamashita, Chapter IV. Examples of a detection method may include: (1) spectroscopic measurement method; (2) fluorescence method; (3) electrode method; and (4) luminescence method. In addition, the method described in *Shin-seikagakujikken koza, tanpakushitsu* V, *Koso meneki sokutei ho*, $3^{rd}$ edition, Enzyme Immunoassay, *Seikagaku jikken ho* (New Biochemical Experiment Course, Protein V, Enzyme Immunoassay, $3^{rd}$ edition, Enzyme Immunoassay, Biochemical Experimental Methods), can also be applied, for example.

When enzyme activity is measured by the fluorescence method, for example, a substrate specific to an enzyme (a substrate, only products decomposed with the enzyme of which emit fluorescence) is allowed to react therewith, and fluorescence in the decomposed products is measured, so as to measure enzyme activity.

When enzyme activity is measured by the spectroscopic measurement method, a difference in spectroscopic properties existing between a substrate and a product is used. A temporal change thereof is measured, and the initial speed of the enzyme reaction is thereby obtained, so as to measure enzyme activity.

When enzyme activity is measured by the electrode method, a method using an automatic titrator is applied. A pH change in a sample solution due to acid or base generated as a result of chemical reactions including an enzyme reaction is electrically detected, so as to measure enzyme activity.

When enzyme activity is measured by the luminescence method, an antibody or antigen has previously been labeled with enzyme. After an antigen-antibody reaction, a chemoluminescent substrate specific to the enzyme (a substrate, only products decomposed with the enzyme of which emit chemoluminescence) is allowed to react therewith, and chemoluminescence in the decomposed products is measured, so as to measure enzyme activity.

When antibody activity is measured using a plastic plate used for ELISA, an antigen of interest is allowed to bind to the inner wall of each well of the plastic plate, and a test sample containing an antibody to be measured is then added thereto for reaction. The antibody binds to the antigen of solid phase. The larger the amount of the antibody contained in the test sample, the higher the binding amount that can be obtained. Thereafter, an anti-immunoglobulin antibody that has been labeled with enzyme is further added thereto. The labeled antibody binds to the above antibody which was bound to the solid phase. The larger the amount of the above antibody, the higher the binding amount of the labeled antibody that can be obtained. An unreacted labeled antibody portion is removed, and a substrate that emits light as a result of the action of the enzyme is then added thereto. Such a substrate emits light depending on the amount of enzyme. Thus, the larger the amount of the enzyme-labeled antibody which was bound to a substrate, the stronger the color tone that is emitted by the substrate. The amount of the antibody contained in the test sample can be obtained by measuring the intensity of the color of the solution with a colorimeter. If a known amount of antibody is diluted stepwise and the amount of each diluted antibody is then measured, the amount of an antibody contained in a test sample can be quantified by comparison with the above obtained values.

When receptor activity is measured, one or more types of receptors or ligands immobilized on a supporting medium are allowed to come into contact with an analyte containing a ligand or receptor that has been labeled with an antigen. Thereafter, the antigen-labeled ligand or receptor which was bound to one or more types of receptors or ligands immobilized on the supporting medium is allowed to come into contact with an antibody reacting with the above antigen (for example, an antibody labeled with enzyme used for detection), so as to carry out an antigen-antibody reaction. Thus, the presence of the antibody bound is detected, thereby detecting a ligand or receptor contained in the analyte.

The present invention will be further specifically described in the following examples. However, these examples are not intended to limit the scope of the present invention.

EXAMPLES (1) Surface Plasmon Resonance Measurement Device and Dielectric Block

Figure 2:
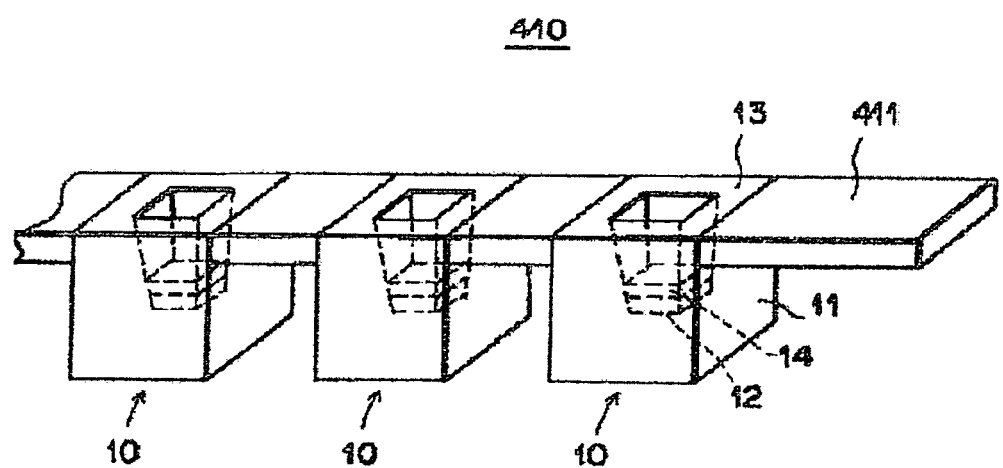
FIG. 2 shows the dielectric block.

The experiments described below were carried out using the device shown in FIG. 22 of Japanese Patent Laid-Open No. 2001-330560 (hereinafter referred to as the surface plasmon resonance measurement device of the present invention), which is shown in FIG. 1 of the present specification, and also using the dielectric block shown in FIG. 23 of the same above publication (hereinafter referred to as the dielectric block of the present invention), which is shown in FIG. 2 of the present specification.

The surface plasmon resonance measurement device shown in FIG. 1 comprises, as a supporting medium for supporting a measurement unit, a slide block 401, which engages in a slidable manner with two guide rods 400, 400 that are disposed in parallel with each other, and flexibly linearly moves along them in the direction of arrow Y in the figure. A precision screw 402 disposed in parallel with the above guide rods 400, 400, is threadably mounted on the above slide block 401. This precision screw 402 is corotated or couterrotated by a pulse motor 403 that constitutes a supporting medium-driving means together with the above screw.

It is to be noted that the driving of the pulse motor 403 is controlled by a motor controller 404. That is to say, an output signal S40 of a linear encoder (not shown), which is incorporated into the slide block 401 to detect the position of the above slide block 401 in the longitudinal direction of the guide rods 400, 400, is inputted to the motor controller 404, and the motor controller 404 controls the driving of the pulse motor 403 based on the signal S40.

A laser light source 31, a condenser lens 32, and a photodetector 40 are disposed on the lower side of the guide rods 400, 400, such that the laser light source 31 and condenser lens 32, and the photodetector 40 sandwich the slide block 401 moving along the guide rods. The condenser lens 32 condenses a light beam 30. In addition, the photodetector 40 is established.

In the present embodiment, a stick-form unit connection body 410 formed by connecting and fixing 8 pieces of measurement unit 10 is used, as an example. Such measurement unit 10 is equipped into the slide block 401 in a state where eight units are disposed in line.

FIG. 2 shows the structure of the unit connection body 410 in detail. As shown in the figure, the unit connection body 410 is formed by connecting 8 pieces of the measurement unit 10 by a connecting member 411.

The measurement unit 10 is formed by molding a dielectric block 11 and a sample-retaining frame 13 using a transparent resin, for example. The measurement unit 10 constitutes an exchangeable measurement chip on a turntable. In order to create such an exchangeable measurement chip on such a turntable, the measurement unit 10 may be fitted into a through-hole formed on the turntable, for example. In the present example, a sensing substance 14 is immobilized on a metal membrane 12.

(2) Measurement Chip

In the following experiment, the measurement chip described in Japanese Patent Application Laid-Open No. 2005-98770 (hydrogel-coated chip) was used. Specifically, a measurement chip coated with hydrogel was produced by the following procedures.

The dielectric block of the present invention, which had been coated with gold via evaporation resulting in a metal membrane with a thickness of 50 nm, was treated with a Model-208 UV-ozone cleaning system (TECHNOVISION INC.) for 30 minutes. Thereafter, a solution that contained 5.0 mM 16-hydroxy-1-hexadecanethiol dissolved in ethanol/water (80/20) was added thereto, such that the solution was allowed to come into contact with the metal membrane. Thus, a surface treatment was carried out at 25° C. for 18 hours. Thereafter, the resultant product was washed with ethanol 5 times, then with a mixed solvent consisting of ethanol and water once, and then with water 5 times.

Subsequently, 10% by weight of epichlorohydrin solution (solvent: a mixed solution consisting of 0.4 M sodium hydroxide and diethylene glycol dimethyl ether at a ratio of 1:1) was allowed to come into contact with the surface coated with 16-hydroxy-1-hexadecanethiol, and the reaction was carried out in a shaking incubator at 25° C. for 4 hours. Thereafter, the surface was washed with ethanol twice and then with water 5 times. Subsequently, 4.5 ml of 1 M sodium hydroxide was added to 40.5 ml of a 25%-by-weight dextran (T500, Pharmacia) aqueous solution, and the thus obtained solution was then allowed to come into contact with the epichlorohydrin-treated surface. Thereafter, the resultant product was incubated in a shaking incubator at 25° C. for 20 hours. The surface was then washed with water at 50° C. 10 times. Subsequently, a mixture obtained by dissolving 3.5 g of bromoacetic acid in 27 g of a 2 M sodium hydroxide solution was allowed to come into contact with the aforementioned dextran-treated surface, and the resultant product was incubated in a shaking incubator at 28° C. for 16 hours. The surface was washed with water, and the aforementioned procedures were repeated once again. The thus obtained sample was defined as a hydrogel-coated measurement chip.

At the same time, a chip used for biosensor that was coated with a hydrophobic polymer (PMMA measurement chip) was produced as follows.

(i) Production of Chip Used for Biosensor Coated with Polymethyl Methacrylate

A cover glass with a size of 1 cm×1 cm, which had been coated with gold via evaporation resulting in a gold film with a thickness of 50 nm, was treated with a Model-208 UV-ozone cleaning system (TECHNOVISION INC.) for 30 minutes. Thereafter, it was placed in a spin coater (MODEL ASS-303; manufactured by ABLE) and then rotated at 1,000 rpm. 50 μl of a methyl ethyl ketone solution containing polymethyl methacrylate (2 mg/ml) was added dropwise to the center of the cover glass coated with gold via evaporation, and 2 minutes later, the rotation was terminated. The thickness of the film was measured by the ellipsometry method (In-Situ Ellipsometer MAUS-101; manufactured by Five Lab). As a result, the thickness of the polymethyl methacrylate film was found to be 20 nm. This sample is called a PMMA surface chip.

(ii) Introduction of COOH Group into PMMA Surface

The cover glass coated with polymethyl methacrylate, as produced above, was immersed in an NaOH aqueous solution (1 N) at 40° C. for 16 hours, followed by washing with water 3 times. This sample is called a PMMA/COOH surface chip.

(iii) Production of Surface Having Linker

The PMMA/COOH surface chip as produced in (ii) above was immersed in 2 ml of a mixed solution of 1-ethyl-2,3-dimethylaminopropylcarbodiimide (400 mM) and N-hydroxysuccinimide (100 mM) for 60 minutes. Thereafter, it was immersed in 2 ml of an α-amino-polyethyleneoxy-ω-carboxylic acid (mean molecular weight: 5,000) aqueous solution (10 mM) for 16 hours. The resultant product was finally washed with water 5 times. This sample is called a PMMA/PEO-C surface chip.

Example 1

Trypsin (manufactured by Worthington) was immobilized on the hydrogel-coated measurement chip produced in (2) above. Measurement was carried out using the surface plasmon resonance measurement device described in (1) above.

(1) Immobilization of Trypsin

A trypsin solution was prepared by dissolving 10 μM leupeptin (manufactured by ICN), a trypsin inhibitor used to prevent autolysis, in the solution with the composition shown in Table 1.

A mixed solution of 1-ethyl-2,3-dimethylaminopropylcarbodiimide (400 mM) and N-hydroxysuccinimide (100 mM) was added to a hydrogel-coated chip, followed by leaving at rest for 20 minutes. Thereafter, the resultant product was washed with a 10 mM phosphate buffer. Subsequently, the aforementioned trypsin solution was added thereto, followed by leaving at rest for the period of time shown in Table 1. Thereafter, the resultant product was subjected to a primary washing with a 10 mM phosphate buffer, and then subjected to a secondary washing with the washing solution shown in Table 1. Thereafter, the resultant product was further washed with a 10 mM phosphate buffer. It is to be noted that it has been known that if such a secondary washing is carried out with 10 mM NaOH, non-specifically adsorbed proteins are washed out, and a baseline drift thereby becomes stable during interaction measurement.

Thereafter, an ethanolamine/HCl solution (1M, pH 8.5) was added to the measurement chip, followed by washing with a 10 mM phosphate buffer, so as to block COOH groups that remained without reacting with trypsin.

By the aforementioned operations, trypsin was immobilized on the surface of the measurement chip via a covalent bond. The amount by which resonance signals (RU value) obtained before the addition of trypsin and after washing had changed was defined as the immobilized amount of trypsin (RU value). Such a trypsin-immobilized amount is shown in Table 1.

(2) Measurement of Biological Activity of Trypsin

Using the chip on which trypsin had been immobilized as described in (1) above, the enzyme activity of trypsin was measured. Since the chip used in the present example has a well-like structure, as shown in FIG. 2, enzyme activity can easily be measured. Specifically, a substrate specific to trypsin (benzoyl-L-arginine-4-methylcoumarin-7-amide (hereinafter referred to as Bz-Arg-MCA); Peptide Institute, Inc.) was allowed to react with trypsin, and fluorescence in the decomposed product was measured.

(3) Reaction of Bz-Arg-MCA

The 10 mM phosphate buffer contained in the measurement chip was removed, and 0.1 mM Bz-Arg-MCA was then added thereto. The reaction was then carried out for 120 minutes.

(4) Fluorescence Measurement

Fluorescence measurement was carried out regarding fluorescence for each of the aforementioned reaction times, using the BMGLabTechnologies FLUOstar measurement device (excitation: 380 nm; and emission: 460 nm). The measurement results are shown in Table 1.

(5) Measurement of Interaction of Compound with Trypsin

The measurement chip was washed with a 10 mM phosphate buffer, and it was then equipped in the surface plasmon resonance device of the present example. Thereafter, leupeptin (0.01 mM; phosphate buffer pH 7.4), the following kinase inhibitor, and an amphipathic compound (0.01 mM; phosphate buffer pH 7.4) were added thereto, followed by leaving at rest for 3 minutes. The amount by which resonance signals (RU value) had changed was defined as the binding amount of the compound. The measurement results are shown in Table 1.

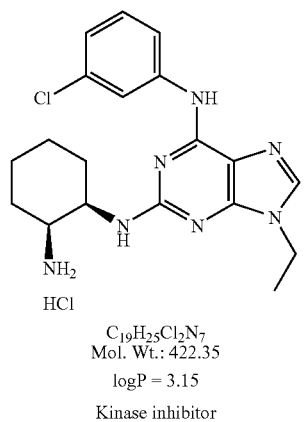

$C_{19}H_{25}Cl_2N_7$
Mol. Wt.: 422.35 logP = 3.15

Kinase inhibitor

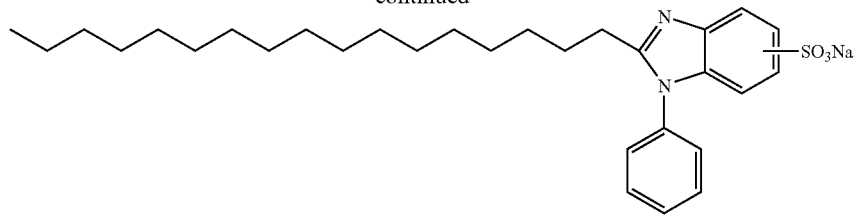

Amphipathic compound

TABLE 1

| Experiment No. | Protein immobilization method | | | | Protein immobilized amount (RU) | Enzyme activity (fluorescence intensity) | Activity value (enzyme activity/ immobilized amount) | Compound binding amount (RU) | | |
|---|---|---|---|---|---|---|---|---|---|---|
| | Immobilization buffer | Protein concentration (mg/ml) | Time (hr) | Secondary washing | | | | Leupeptin | Kinase inhibitor | Amphipathic compound |
| 1 | Phosphate buffer (pH 7.4) | 10 | 1 | Phosphate buffer (pH 7.4) | 4150 | 230 | 0.055 | 25 | 19 | 37 |
| 2 | Phosphate buffer (pH 7.4) | 2 | 1 | Phosphate buffer (pH 7.4) | 2580 | 615 | 0.238 | 19 | 1 | 1 |
| 3 | Phosphate buffer (pH 7.4) | 2 | 1 | 10 mM NaOH | 2310 | 370 | 0.160 | 8 | 5 | 13 |
| 4 | Acetate buffer (pH 5.0) | 0.1 | 0.2 | Phosphate buffer (pH 7.4) | 5200 | 40 | 0.008 | 16 | 21 | 51 |

There have been the following two conventional methods of selecting an immobilization method:

(1) a method of selecting an immobilization method involving the largest amount of a protein immobilized; and (2) a method of selecting an immobilization method involving the largest binding amount of a compound that specifically binds.

If the method described in (1) above is applied to the obtained results, the method of experiment No. 4 is selected. On the other hand, if the method described in (2) above is applied, the method of experiment No. 1 is selected. However, as is clear from the enzyme activity values shown in Table 1, in the methods of experiment Nos. 1 and 4, enzyme activity has been significantly decreased. As is clear from the binding amount of a kinase inhibitor or an amphipathic compound, a hydrophobic compound is easily non-specifically adsorbed on the surface of experiment No. 1 or 4. Thus, it can be said that it is highly likely that the binding of leupeptin is also a non-specific binding. It can be concluded that in the present experiment, the method of experiment No. 2, wherein a specific inhibitor, leupeptin binds to the surface, whereas a compound having no inhibitory ability does not bind thereto, provides the most suitable surface for the measurement of interaction with the compound.

Example 2

Trypsin (manufactured by Worthington) was immobilized on the PMMA measurement chip of the present example. Measurement was carried out using Biacore 3000 (manufactured by Biacore).

(1) Immobilization of Trypsin

The PMMA measurement chip was equipped in Biacore 3000, and trypsin was then immobilized on the chip under the same conditions as those described in Example 1.

(2) Measurement of Biological Activity of Trypsin

Using the chip on which trypsin had been immobilized in (1) above, the enzyme activity of trypsin was measured by the following method. The chip was equipped in SurfacePrepUnit (manufactured by Biacore), and the surface of the chip was washed with a 10 mM phosphate buffer 3 times. Thereafter, 2 μl of 0.1 mM Bz-Arg-MCA was poured therein, and it was left for 120 minutes. Thereafter, it was recovered.

(3) Fluorescence Measurement

Fluorescence measurement was carried out regarding each reaction time, using the BMGLabTechnologies FLUOstar measurement device (excitation: 380 nm; and emission: 460 nm).

(4) Measurement of Interaction of Compound with Trypsin

A leupeptin solution (0.002 mM; HBS-N buffer) was added, and the reaction was then carried out for 10 minutes. Thereafter, the amount by which resonance signals (RU value) had changed was defined as the amount of leupeptin (manufactured by ICN) binding to trypsin.

The measurement chip was washed with a 10 mM phosphate buffer, and it was then equipped in Biacore 3000. Thereafter, leupeptin (0.01 mM; phosphate buffer pH 7.4), the following kinase inhibitor, and an amphipathic compound (0.01 mM; phosphate buffer pH 7.4) were poured therein, followed by leaving at rest for 3 minutes. The amount by which resonance signals (RU value) had changed was defined as the binding amount of the compound.

(5) Measurement Results

The same conclusion as obtained in Example 1 was obtained.

INDUSTRIAL APPLICABILITY

The measurement method of the present invention enables the measurement of the amount of the immobilized protein and the measurement of the biological activity thereof. In addition, by measuring the interaction of a compound with the immobilized protein that maintains certain activity by the present measurement method, it becomes possible to accurately analyze a compound interacting with the protein.

The invention claimed is:

1. A measurement method using a biosensor substrate, comprising:
   (i) a step of measuring the amount of a physiologically active substance immobilized on the substrate and
   (ii) a step of measuring the biological activity of the physiologically active substance immobilized on the substrate, wherein both the amount in step (i) and the activity in step (ii) are measured on said same biosensor substrate.

2. The measurement method according to claim 1, wherein the physiologically active substance is a protein.

3. The measurement method according to claim 1, wherein the physiologically active substance is an enzyme.

4. The measurement method according to claim 1, wherein the amount of the physiologically active substance immobilized on the substrate is measured by surface plasmon resonance analysis.

5. The measurement method according to claim 4, wherein the surface plasmon resonance analysis is carried out using a biosensor used for a surface plasmon resonance measurement device comprising a dielectric block, a metal film formed on a face of the dielectric block, a light source for generating a light beam, an optical system for allowing said light beam to enter said dielectric block such that total reflection conditions can be obtained at the interface between said dielectric block and said metal film and that components at various incident angles can be contained, and a light-detecting means for detecting the state of surface plasmon resonance by measuring the intensity of the light beam totally reflected at said interface, wherein said biosensor is composed of said dielectric block and said metal film, wherein said dielectric block is formed as one block comprising the entirety of the entrance face and exit face of said light beam and a face on which said metal film is formed, and said metal film is integrated with the dielectric block.

6. The measurement method according to claim 1, wherein the biological activity of the physiologically active substance is measured by spectroscopic measurement.

7. The measurement method according to claim 1, which comprises:
   (1) a step of confirming the biological activity value per unit quantity of a physiologically active substance immobilized on a substrate, which is represented by the following formula 1, based on the amount of the physiologically active substance immobilized on the substrate and the biological activity value of the physiologically active substance immobilized on said substance, which are measured on the same biosensor substrate, (biological activity value per unit quantity of physiologically active substance immobilized)=(biological activity value of physiologically active substance immobilized on substrate)/(amount of physiologically active substance immobilized on substrate);     Formula 1 and
   (2) a step of detecting or measuring the interaction of the physiologically active substance with a test substance using the substrate on which the physiologically active substance has been immobilized by the immobilization method confirmed in said step (1).

8. The measurement method according to claim 1, which comprises:
   (1) a step of optimizing a method of immobilizing a physiologically active substance on a biosensor substrate, using, as an indicator, the biological activity value per unit quantity of the physiologically active substance immobilized on a substrate, which is represented by the following formula 1, based on the amount of the physiologically active substance immobilized on the substrate and the biological activity value of the physiologically active substance immobilized on said substance, which are measured on the same biosensor substrate, (biological activity value per unit quantity of physiologically active substance immobilized)=(biological activity value of physiologically active substance immobilized on substrate)/(amount of physiologically active substance immobilized on substrate);     Formula 1 and
   (2) a step of detecting or measuring the interaction of the physiologically active substance with a test substance, using the substrate on which the physiologically active substance has been immobilized by the immobilization method optimized in said step (1).

9. The measurement method according to claim 7, wherein the measurements of the amount of a physiologically active substance immobilized on a substrate and the biological activity value of the physiologically active substance immobilized on said substrate in step (1), and the detection or measurement of the interaction of the physiologically active substance with a test substance in step (2), are carried out on the same biosensor substrate.

10. The measurement method according to claim 8, wherein the measurements of the amount of a physiologically active substance immobilized on a substrate and the biological activity value of the physiologically active substance immobilized on said substrate in step (1), and the detection or measurement of the interaction of the physiologically active substance with a test substance in step (2), are carried out on the same biosensor substrate.

* * * * *